United States Patent
McKendry et al.

(10) Patent No.: US 7,061,239 B2
(45) Date of Patent: Jun. 13, 2006

(54) METHOD FOR MAGNETIC FIELD TRACKING IN A NMR CHECK WEIGHING SYSTEM

(75) Inventors: James M. McKendry, Headington (GB); Robert Selway, Kidlington (GB); Jozef A. W. M. Corver, Nuenen (NL)

(73) Assignee: The BOC Group, Inc., Murray Hill, NJ (US)

( * ) Notice: Subject to any disclaimer, the term of this patent is extended or adjusted under 35 U.S.C. 154(b) by 0 days.

(21) Appl. No.: 10/836,797

(22) Filed: Apr. 30, 2004

(65) Prior Publication Data

US 2005/0242808 A1    Nov. 3, 2005

(51) Int. Cl.
*G01V 3/00* (2006.01)

(52) U.S. Cl. ...................................... 324/307; 324/309
(58) Field of Classification Search ................ 324/300, 324/306, 307, 309, 313, 303
See application file for complete search history.

(56) References Cited

U.S. PATENT DOCUMENTS

| | | | |
|---|---|---|---|
| 3,796,873 A | 3/1974 | Ledgett | |
| 3,810,001 A * | 5/1974 | Ernst | 324/313 |
| 4,536,711 A * | 8/1985 | King et al. | 324/306 |
| 4,727,325 A | 2/1988 | Matsui et al. | |
| 5,015,954 A | 5/1991 | Dechene et al. | |
| 5,049,819 A | 9/1991 | Dechene et al. | |
| 5,291,422 A | 3/1994 | Esztergar | |
| 5,302,894 A | 4/1994 | Hrubes | |
| 5,302,896 A * | 4/1994 | Dechene et al. | 324/307 |
| 5,302,897 A * | 4/1994 | Tache et al. | 324/307 |
| 5,367,260 A * | 11/1994 | Dechene et al. | 324/307 |
| 5,408,181 A * | 4/1995 | Dechene et al. | 324/307 |
| 5,530,350 A * | 6/1996 | Dechene et al. | 324/306 |
| 5,596,275 A * | 1/1997 | Busch | 324/307 |
| 6,028,428 A | 2/2000 | Cunningham et al. | |
| 6,194,898 B1 * | 2/2001 | Magnuson et al. | 324/300 |
| 6,333,629 B1 * | 12/2001 | Pykett et al. | 324/307 |
| 6,362,619 B1 | 3/2002 | Prammer et al. | |
| 6,377,049 B1 | 4/2002 | Benz et al. | |
| 6,426,058 B1 | 7/2002 | Pines et al. | |
| 6,452,390 B1 * | 9/2002 | Wollin | 324/306 |
| 6,946,838 B1 * | 9/2005 | Corver et al. | 324/307 |
| 2004/0231699 A1 | 11/2004 | Corver | |

(Continued)

FOREIGN PATENT DOCUMENTS

DE    1803372 A1    5/1970

(Continued)

OTHER PUBLICATIONS

Derwent WPI Abstract, UNILEVER NV, Package Weight Measuring System, NL 154001B, Jul. 15, 1977 (Corresponds to DE 1803372A1).

*Primary Examiner*—Diego Gfutierrez
*Assistant Examiner*—Tiffany A. Fetzner
(74) *Attorney, Agent, or Firm*—Ira L. Zebrak; Bernard Lau

(57) ABSTRACT

A method (10) insures that the characteristics of the magnetic field used in a magnetic resonance check weighing system (20) for samples in vials (22) on a production line track deviations from the resonant frequency of the sample. The method (10) includes the steps of obtaining (50) a free induction decay signal from a magnetic resonance measurement of the sample, monitoring (52) from the free induction decay signal the deviation of the resonance frequency of the magnetic resonance measurement from a preselected resonance frequency; and adjusting (62) the magnetic field to maintain the preselected resonance frequency.

8 Claims, 2 Drawing Sheets

U.S. PATENT DOCUMENTS

2004/0251904 A1* 12/2004 Corver et al. ............... 324/321
2005/0116712 A1* 6/2005 Corver et al. ............... 324/309
2005/0122104 A1* 6/2005 Corver et al. ............... 324/309
2005/0242808 A1* 11/2005 McKendry et al. ......... 324/307

FOREIGN PATENT DOCUMENTS

| GB | 2149509 A | 6/1985 |
|---|---|---|
| WO | WO 99/67606 A1 | 12/1999 |

* cited by examiner though not illustrated, and the present invention is not

METHOD FOR MAGNETIC FIELD TRACKING IN A NMR CHECK WEIGHING SYSTEM

FIELD OF THE INVENTION

The present invention relates to check weighing material in a container, while the container is moving in a production line, using nuclear magnetic resonance (NMR) techniques. More particularly, the present invention relates to a method for maintaining the magnetic field used for NMR measurement substantially constant.

BACKGROUND

The use of NMR techniques in measurement, detection and imaging has become desirable in many scientific fields of endeavor. The non-invasive, non-destructive nature of NMR has facilitated application to industrial instrumentation, analysis and control tasks, in a variety of applications, including but not limited to cosmetics, perfumes, industrial chemicals, biological samples and food products. As one example, check weighing is used by the pharmaceuticals industry for monitoring and regulating the amount of drug in a sealed glass vial during filling. The drug weight can be as small as a fraction of a gram, and is required to be weighed with an accuracy of a few percent or better, in a vial weighing tens of grams at a rate of several weighings per second.

International Patent Application No. WO 99/67606, incorporated herein by reference as if fully written out below, describes a check weighing system for samples on a production line using NMR techniques. This system includes a magnet for creating a static magnetic field over an interrogation zone to produce a net magnetisation within a sample located within the interrogation zone, and a RF coil for applying an alternating magnetic field over the interrogation zone to cause excitation of the sample according to the principles of NMR.

As is well known in the NMR art, after pulse excitation of the sample by the alternating magnetic field, the sample emits a signal induced in the RF coil, called the free induction decay ("FID"), from which much information, like sample mass (or weight) can be learned. The FID is directly proportional to the net magnetisation applied to the sample. Consequently, any variation in the applied magnetisation produces changes in the FID, including its frequency and spatial orientation, and effects the determination of sample weight obtained from the FID. When a single NMR measurement is being made, a NMR spectrometer may be manually calibrated and proper results achieved. However, when multiple NMR measurements are being made over time, as is the case when weight checking of containers in a production line is in continuous operation, the magnetic fields drift because of temperature variations in the magnets used to generate those magnetic fields. Thus, in such applications it is imperative to monitor and correct for variations in the magnetic fields. Adjusting the NMR magnetic field in this manner insures that the resonance frequency remains at the resonant frequency of the sample, and improves the accuracy and precision of the determined weight.

It is desirable to provide a method for insuring that the characteristics of the magnetic field used in a NMR check weighing system for samples on a production line track deviations from the resonant frequency of the sample.

SUMMARY

There is provided a method for use in a magnetic resonance check weighing system for samples on a production line, the magnetic resonance check weighing system having a magnetic field, including the steps of:

obtaining a free induction decay signal from a magnetic resonance measurement of the sample, monitoring from the free induction decay signal the deviation of the resonance frequency of the magnetic resonance measurement from a preselected resonance frequency; and adjusting the magnetic field to maintain the preselected resonance frequency.

DETAILED DESCRIPTION

Figure 2:
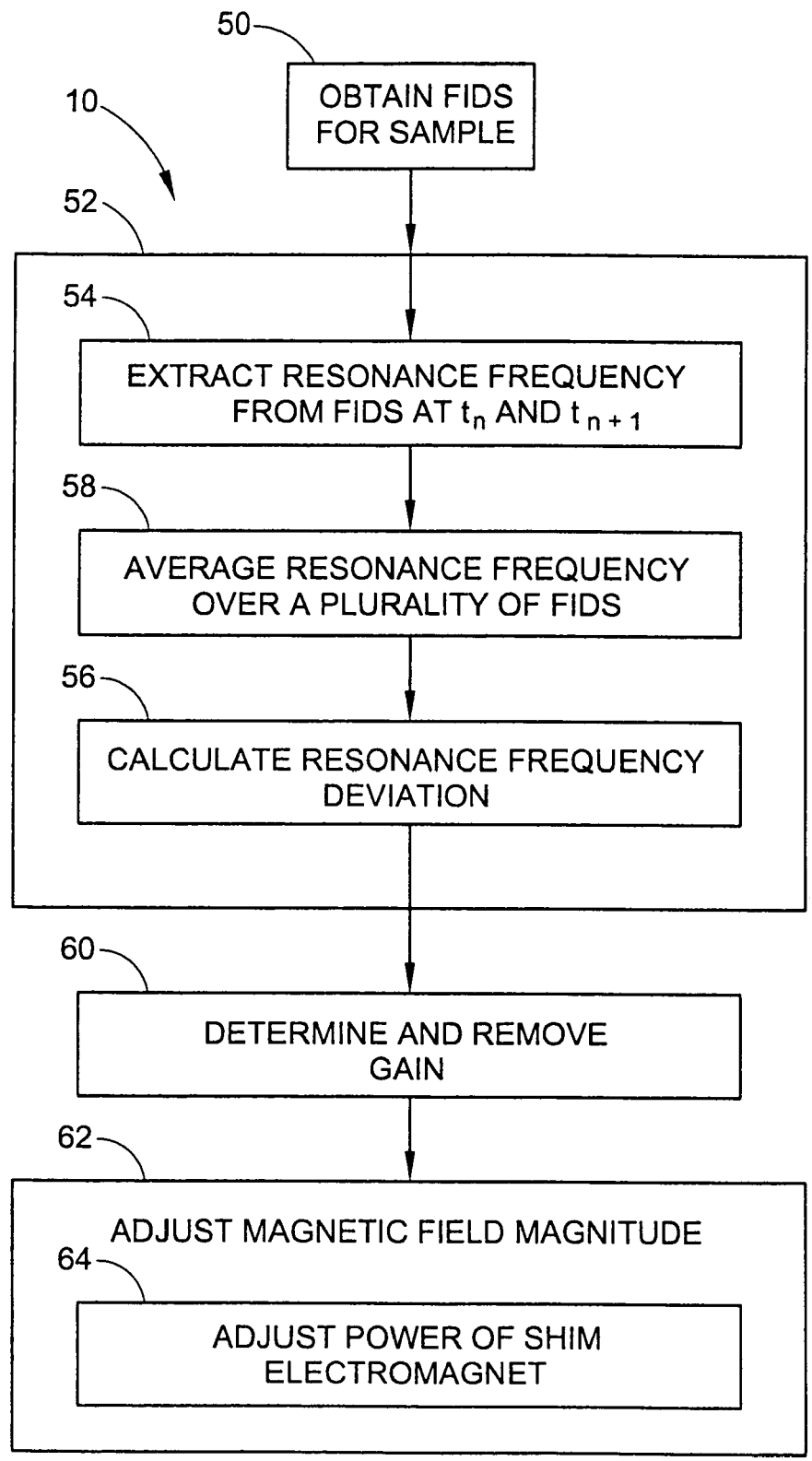
FIG. 2 is a top level flow chart of an exemplary method in accordance with the teachings of the present invention for magnetic field tracking in a NMR check weighing system for samples on a production line.

A method in accordance with the present invention is indicated generally by the numeral 10 in FIG. 2. This method is used in a non-contact, NMR check weighing system 20 that checks the mass (or weight) of the content of a container while continuously moving in a production line. One exemplary application requiring such check weighing is the packaging of pharmaceuticals. In order to understand best this method, it is helpful to first review certain of the structure of an exemplary NMR check weighing system and its associated production line.

Exemplary NMR Check Weighing System for Pharmaceutical Packaging

Figure 1:
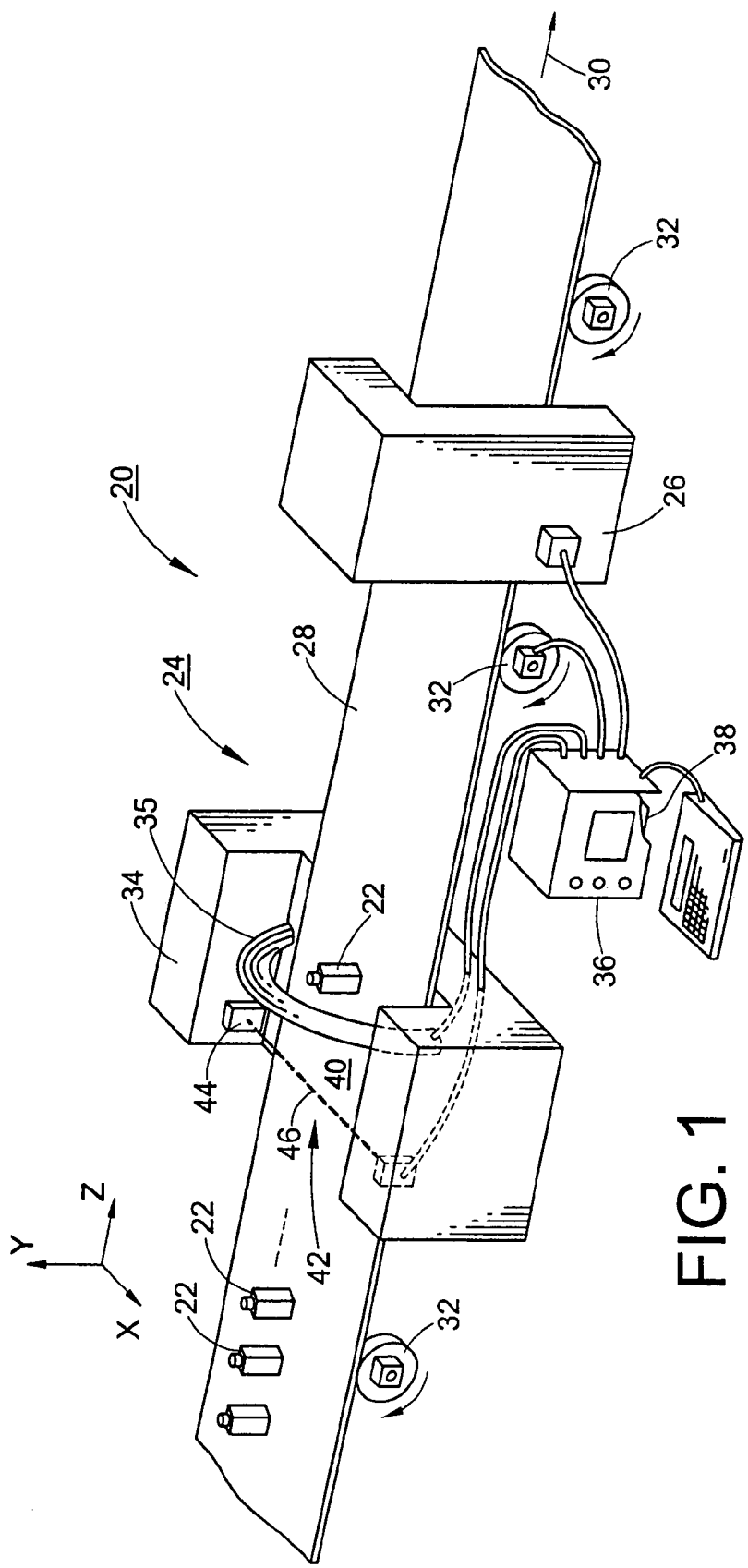
FIG. 1 is a perspective view of a portion of a production line with an exemplary NMR check weighing station for checking that each container passing through the weighing station has the desired amount of product.

FIG. 1 shows a portion of a production line, which fills glass vials 22 with a drug sample. The exemplary check weighing station 24 is provided "in-line" for non-contact weighing of each of the filled vials that pass therethrough, and a reject station 26 that removes those vials from the line that do not have the sufficient amount of the drug to meet product specifications. Vials 22 are transported to check weighing station 24 from a filling (and optionally sealing) station (not shown) by a conveyor having a conveyor belt 28 which, as represented by the arrow 30, moves in the z direction through the action of rotating conveyor wheels 32.

Check weighing station 24 uses NMR techniques to determine the mass of the drug sample within each of the vials 22. As those ordinarily skilled in the art will appreciate, glass vials are useful as the container, because they do not give a signal that might interfere with the measurement process. In this embodiment, check weighing station 24 includes a permanent magnet 34, RF probe 35 (shown diagrammatically in FIG. 1), and a computer control system 36 having a processor 38. Magnet 34 creates a homogeneous direct current (DC) or static magnetic field in the x direction across conveyor belt 28 in a region that may be referred to as the interrogation zone 40. Interrogation zone 40 extends the length of conveyor belt 28 through which the static magnetic field is uniformly applied by permanent magnet 34. The sample in vial 22 contains nuclei which each possess a magnetic moment, e.g. 1H nuclei (protons), as a result of the spin of the nuclei. Because the sample protons posses a magnetic moment, the sample is capable of acquiring a net magnetisation when under the influence of certain magnetic fields. When the sample is within interrogation zone 40, the applied static magnetic field creates a net magnetisation within the sample. A vial position detection device 42 preceding or at the start of interrogation zone 40 (such as the optical position sensor 44 having a light beam 46) accurately and precisely detects when vial 22 reaches a known physical position on conveyor belt 28 preceding check weighing station 24.

In most NMR systems, the static magnetic field strength is such that the Larmor frequency of the sample is in the radio frequency range of the electromagnetic spectrum. Applying an alternating current (AC) magnetic field to the sample at the sample's Larmor frequency and orientated orthogonal to the static magnetic field, will cause the sample's net magnetisation to rotate about the AC magnetic field's axis, away from the direction of the static field. In this embodiment, this magnetic field is generated by applying a corresponding AC current to the RF probe 35. Varying the amount of energy delivered to the RF probe 35 can vary the angle of rotation of the net magnetisation.

In this exemplified embodiment, an excitation field that causes a 90° rotation is used to excite the sample. After the 90° pulse has been applied to the sample, the sample is left in a high-energy, non-equilibrium state, from which it will relax back to its original state of equilibrium. As it relaxes, electromagnetic energy at the Larmor frequency is emitted, the magnetic component of which induces a sample reply signal known as the Free Induction Decay ("FID") in the form of current in the RF probe 35.

RF probe 35 monitors energy emitted by the sample as the net magnetisation of the sample returns to its original state and generates an output signal having a characteristic which is proportional to the energy emitted. In the present example a characteristic of the induced current, i.e., amplitude, varies with, among other things, the number of magnetic moments in the sample and hence the number of molecules in the sample. The received signal is then passed to the computer control system 36, which compares the amplitude of the signal received from the unknown sample, with the amplitude of a signal received from a calibration sample with a known mass (or weight), to determine the mass (or weight) of the sample being tested.

For illustrative purposes, but not by way of limitation, the general operation of the NMR check weighing system 24 as shown in FIG. 1 will be described. First, check weighing system 24 is initialized, including installing a RF probe 35 appropriate for the sample to be tested. Once production is begun, conveyor belt 28 continuously transports vials 22 whose sample mass (or weight) is to be determined. As each vial 22 reaches a position detected by optical position sensor 44, optical position sensor 44 generates a signal accurately establishing the position of that vial 22 to computer control system 36. Computer control system 36 then tracks the motion of conveyor belt 28 as vial 22 advances to the position $P_M$ within interrogation zone 40 where the sample in vial 22 will return the maximum sample reply signal.

At the instant in time when vial 22 is in position $P_M$, a brief energization of RF probe 35 is triggered, applying an alternating magnetic field in interrogation zone 40 such that the net magnetisation of the sample in vial 22 is temporarily changed. RF probe 35 monitors the energy emitted by the sample in vial 22 as the net magnetisation of the sample returns to its original state of equilibrium, and generates an output signal having a characteristic which is proportional to the energy emitted, such as current amplitude. Computer control system 36 receives the RF probe 35 output signal. Processor 38 compares the current amplitude or other output signal characteristic with like data obtained from at least one similar sample of known mass, and determines the mass of the sample from the results of the comparison.

Magnetic Field Tracking

FIG. 2 depicts a top level flow chart of an exemplary method in accordance with the teachings of the present invention for magnetic field tracking in a NMR check weighing system for samples on a production line.

The skilled artisan will understand that most NMR spectrometers digitize and store FID signal data each time a NMR measurement is performed. As a result, in the first step 50 shown in FIG. 2 the relevant FID data from a magnetic resonance measurement of a first sample in vial 22 is obtained by processor 38, such as by retrieving it from memory.

Next, in step 52 (shown in FIG. 2 as the box enclosing steps 54, 56, and optional step 58), processor 38 continuously monitors from the FID the deviation of the resonance frequency of the magnetic resonance measurement from a pre-selected or base resonance frequency, the resonant frequency of the sample under test, i.e. one of the production samples. Step 52 includes, extracting the resonance frequency from at least two FIDs (in step 54), and calculating the deviation of the resonance frequency of the magnetic resonance measurement from the pre-selected resonance frequency (in step 56). Optionally, in order to reduce the effects of noise from both external and internal sources, in step 58-resonance frequency data extracted from the FIDs may be smoothed such as by averaging values over a plurality of magnetic resonance measurements of the sample under test. Of course, smoothing resonance frequency values must occur after such data is obtained and before deviation of the resonance frequency is calculated. Deviation of the resonance frequency may be calculated from the rate of change of the resonance frequency, as known to the ordinarily skilled artisan.

As explained above, method 10 causes the magnetic field to continuously monitor deviations in the resonance frequency. Consequently, at least one characteristic of the magnetic field must be adjusted. The adjusting device may introduce an electrical signal gain factor into the adjustment of the magnetic field. In step 60, any gain effects are removed before the magnetic field is adjusted. This may be accomplished by any of the recognized techniques known in the art, such as extracting the resonance frequencies for operation at maximum and minimum field strengths, calculating a "full scale" resonance frequency difference, and applying to each magnetic field adjustment a correction factor that is a ratio of the change in resonance frequency with the full scale resonance frequency difference.

In step 62 the previously mentioned tracking adjustment of a magnetic field characteristic, such as magnitude of the main magnetic field, is carried out. The skilled artisan will appreciate a variety of methods by which magnetic field adjustment may be accomplished. Perhaps the most simple is to adjust, in step 64, one or more so-called shim electromagnets commonly included on NMR spectrometers by varying the output value from the digital to analog converter typically provided to control the magnitude (power) of the magnetic field generated by the shim electromagnet. Altering the spatial orientation of the position of the sample under test to the magnetic field is also capable of providing the necessary magnetic field adjustment. For example, the poles of a magnet might be moved closer together or further apart. Additionally, the location of other components of NMR check weighing system 20 such as RF coil 35 might be moved.

It will be understood that the embodiments described herein are merely exemplary and that a person skilled in the art may make many variations and modifications without departing from spirit and scope of the invention. The various embodiments may be practiced in the alternative, or in combination, as appropriate. All such modifications and variations are intended to be included within the scope of the invention as defined in the appended claims.

We claim:

1. A method for use in a magnetic resonance check weighing system that is configured for individual production samples on a production line, the magnetic resonance check weighing system having at least one magnetic field, comprising the steps of:

obtaining a free induction decay signal from a magnetic resonance measurement of a first sample;

obtaining a free induction decay signal from a magnetic resonance measurement for each of a plurality of production samples;

continuously monitoring from the free induction decay signals of each of a plurality of production samples, during check weighing of the plurality of production samples, the deviation of the resonance frequency of the magnetic resonance measurements from a pre-selected resonance frequency; and adjusting the at least one magnetic field of the magnetic resonance check weighing system in order to maintain the pre-selected resonance frequency.

2. The method according to claim 1, wherein said step of continuously monitoring the free induction decay signals includes the steps of extracting the resonance frequency from the free induction decay signal for each of the plurality of production samples, and calculating the deviation of the resonance frequency for each of the magnetic resonance measurements from the pre-selected resonance frequency.

3. The method according to claim 2, wherein said step of extracting the resonance frequency includes the step of adjusting a resonance frequency value over a plurality of magnetic resonance measurements for the plurality of production samples.

4. The method according to claim 1, wherein the magnetic resonance check weighing system includes a shim electromagnet in order to adjust the at least one magnetic field, and said step of adjusting the at least one magnetic field includes the step of adjusting the shim electromagnet.

5. The method according to claim 4, wherein the step of adjusting the shim electromagnet includes the step of adjusting a value processed by a digital to analog converter controlling the at least one magnetic field generated by the shim electromagnet.

6. The method according to claim 1, wherein the magnetic resonance check weighing system includes a plurality of magnets and other components, and said step of adjusting the at least one magnetic field includes the step of adjusting the spatial orientation of one of the plurality of magnets and other components.

7. The method according to claim 1, wherein the at least one magnetic field is operated by a device having an electrical signal gain, and said step of adjusting the at least one magnetic field further includes the step of determining and removing the gain before said step of adjusting the at least one magnetic field.

8. The method according to claim 1, wherein said step of continuously monitoring the free induction decay signals includes the steps of extracting the resonance frequency from the free induction decay signal for each of the plurality of production samples, averaging the resonance frequency over a plurality of free induction decay signals, and calculating the deviation of the resonance frequency from each of the magnetic resonance measurements from the pre-selected resonance frequency.

* * * * *